(12) United States Patent
Wilcox

(10) Patent No.: US 9,744,676 B2
(45) Date of Patent: Aug. 29, 2017

(54) DUAL SIDE ACTING HYDRAULIC GRIPS SYNCHRONIZATION

(75) Inventor: Joseph Wilcox, Fredonia, PA (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 773 days.

(21) Appl. No.: 13/502,888

(22) PCT Filed: Sep. 30, 2010

(86) PCT No.: PCT/US2010/050845
§ 371 (c)(1),
(2), (4) Date: Apr. 19, 2012

(87) PCT Pub. No.: WO2011/049726
PCT Pub. Date: Apr. 28, 2011

(65) Prior Publication Data
US 2012/0205930 A1    Aug. 16, 2012

Related U.S. Application Data

(60) Provisional application No. 61/253,139, filed on Oct. 20, 2009.

(51) Int. Cl.
*B25B 1/02*   (2006.01)
*B25J 15/02*  (2006.01)
*G01N 3/04*   (2006.01)

(52) U.S. Cl.
CPC ............ *B25J 15/0253* (2013.01); *G01N 3/04* (2013.01); *G01N 2203/0405* (2013.01); *G01N 2203/0411* (2013.01)

(58) Field of Classification Search
USPC ................ 269/32, 20, 24, 27, 228, 143, 249
See application file for complete search history.

(56) References Cited

U.S. PATENT DOCUMENTS

| 3,375,710 A |   | 4/1968 | Cavanaugh et al. |
| 4,430,997 A | * | 2/1984 | DiGiovanni ......... A61B 17/128 606/143 |
| 4,696,503 A |   | 9/1987 | Collodel |
| 4,735,452 A | * | 4/1988 | Nemoto ............... B25J 15/0273 294/119.1 |
| 5,224,747 A | * | 7/1993 | Tsuchiya ............... B23Q 7/043 279/110 |

(Continued)

FOREIGN PATENT DOCUMENTS

| EP | 1245346 | 10/2002 |
| WO | 2007120784 | 10/2007 |

OTHER PUBLICATIONS

ISR for PCT/US2010/050845 dated Feb. 11, 2011.

*Primary Examiner* — Larry E Waggle, Jr.
*Assistant Examiner* — Alvin Grant
(74) *Attorney, Agent, or Firm* — McCarter & English, LLP

(57) ABSTRACT

A synchronized gripping mechanism is provided which includes coupled slider-crank mechanisms. The coupled mechanisms each include a sliding grip and an intermediate link connected by a pivotal connector. A coupler link is provided on a stationary pivot and which couples and synchronizes the two slider-crank mechanisms. Overload protection structure is provided to prevent damaging the links if one of the sliding grips encounters an off-center specimen.

20 Claims, 7 Drawing Sheets

(56) References Cited

U.S. PATENT DOCUMENTS

| | | | | |
|---|---|---|---|---|
| 5,588,688 A | * | 12/1996 | Jacobsen | A61F 2/588 |
| | | | | 294/106 |
| 5,755,475 A | * | 5/1998 | Zajac, Jr. | B25J 15/0253 |
| | | | | 294/119.1 |
| 5,938,257 A | * | 8/1999 | Blatt | B25J 15/0273 |
| | | | | 294/119.1 |
| 6,234,550 B1 | * | 5/2001 | Stoltenhoff | B65G 1/0435 |
| | | | | 294/119.1 |
| 6,412,845 B1 | * | 7/2002 | Sawdon | B25B 5/122 |
| | | | | 294/198 |
| 7,197,963 B1 | | 4/2007 | Flud | |
| 7,695,234 B2 | * | 4/2010 | Yamashita | H01L 21/67769 |
| | | | | 187/411 |
| 8,414,044 B2 | * | 4/2013 | Weber | B25J 15/0266 |
| | | | | 294/119.1 |
| 8,474,806 B2 | * | 7/2013 | Orgeron | B25B 5/061 |
| | | | | 269/218 |
| 8,561,973 B2 | * | 10/2013 | Martin | E05C 19/14 |
| | | | | 269/201 |
| 2001/0024045 A1 | | 9/2001 | Bertini | |
| 2004/0089126 A1 | * | 5/2004 | McLean | B26D 1/08 |
| | | | | 83/605 |

* cited by examiner

DUAL SIDE ACTING HYDRAULIC GRIPS SYNCHRONIZATION

This application is national phase of PCT/US2010/050845 filed Sep. 30, 2010, and claims priority to U.S. Provisional Patent Application No. 61/253,139, filed on Oct. 20, 2009 on behalf of Joseph Wilcox, titled "Dual Side Acting Hydraulic Grips Synchronization."

BACKGROUND

Field of the Disclosed Embodiments

The disclosed embodiments relate generally to hydraulic grips and specifically to hydraulic grips for material testing, where the grips have gripping members which are synchronized by being connected to a common link.

Background of the Disclosed Embodiments

Several companies currently manufacture various styles of synchronized power grips. Systems utilizing a pair of such grips will grip a specimen and apply tension to the specimen for the purpose of testing the stress/strain characteristics of the specimen. Notable grip manufacturers are Zwick and Demgen, both of Germany. These companies offer grips that are mechanically and hydraulically synchronized. The mechanically synchronized offerings make use of known rack and pinion gear systems for synchronizing the grips.

Systems using a rack and pinion configuration often have performance limitations related to strength and durability of the synchronization mechanism. In the presence of contamination, the rack and pinion interface is susceptible to diminished performance. The synchronizer components in a rack and pinion system are typically complicated to manufacture, assemble and adjust. This creates difficulty with maintenance and serviceability and often requires the grips to be pulled from operation and returned to the manufacturer for repair.

Systems using a rigidly coupled mechanical synchronization offer no protection from overloading. Such systems are limited to testing situations that do not produce a clamping load biased towards one half of the gripping tool, for example, when attempting to clamp a bent specimen. Without overload protection, the unequal clamping load transmitted to the synchronization mechanism can result in diminished performance and component failure.

In contrast, hydraulically synchronized systems typically lack the precision necessary to provide accurate and repeatable on center clamping. Another characteristic of hydraulic systems is the need to frequently resynchronize the system through a time consuming procedure.

In view of the stated shortcomings of known gripping mechanisms, it is an object of the disclosed embodiments to provide a design for synchronizing dual side acting specimen grips used for materials testing. The disclosed embodiments should provide precise and repeatable on center clamping, an ability to function continually in a contamination filled environment, should require minimal maintenance with field serviceability, and provide an overall robust design capable of withstanding the loads associated with high capacity materials testing.

SUMMARY OF THE INVENTION

In view of the stated objects, a synchronized gripping mechanism is provided which includes coupled slider-crank mechanisms. The coupled mechanisms each include a sliding grip and an intermediate link connected by a pivotal connector. A coupler link is provided on a stationary pivot and which couples and synchronizes the two slider-crank mechanisms. Overload protection structure is provided to prevent damaging the links if one of the sliding grips encounters an off-center specimen.

BRIEF DESCRIPTION OF THE FIGURES

Certain embodiments of the invention will be described through the use of the accompanying drawings, which are not to be considered as limiting, and in which.

DETAILED DESCRIPTION OF THE DISCLOSED EMBODIMENTS

Figure 1:
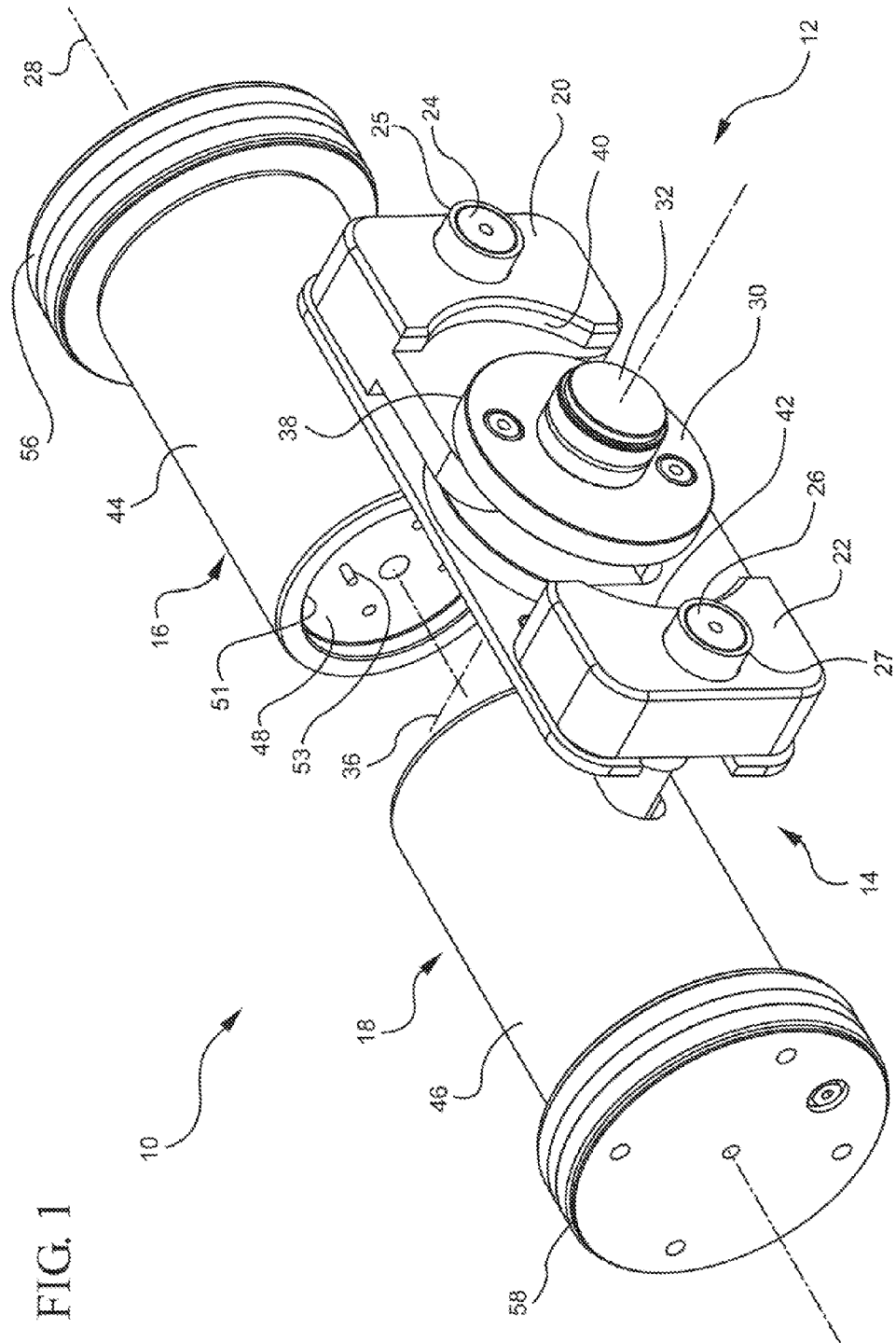
FIG. 1 illustrates a side perspective view of coupled slider-link mechanisms according to the disclosed embodiments.
Figure 2:
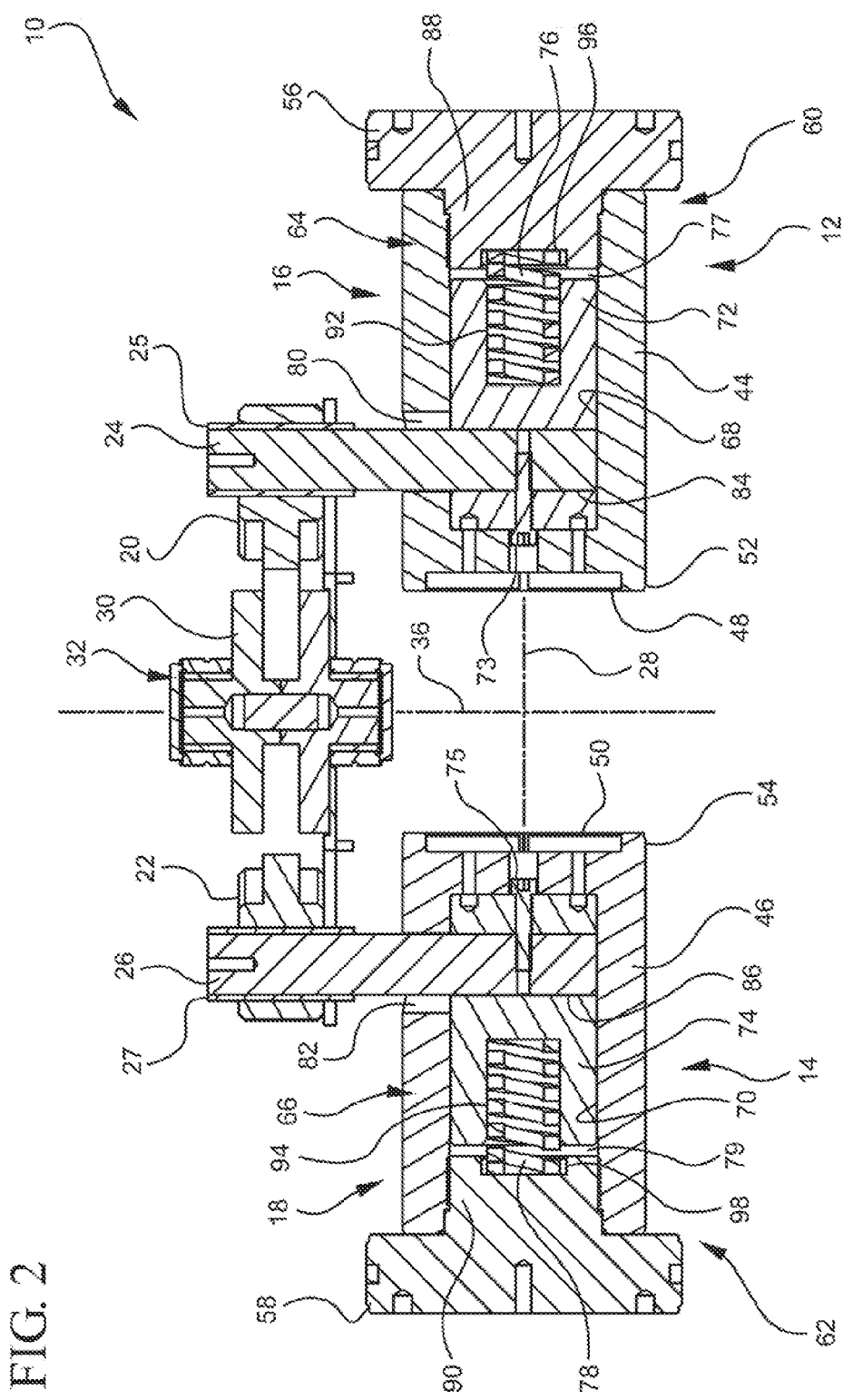
FIG. 2 illustrates a cross sectional view of the linkage illustrated in FIG. 1, exposing overload protection structure contained within the linkage.

Turning to FIGS. 1 and 2, there is illustrated a synchronized gripping mechanism 10 according a disclosed embodiment. The gripping mechanism includes first and second slider-crank mechanisms 12, 14, which are based on a four-bar linkage.

The slider-crank mechanisms 12, 14 include respective first and second cylindrically shaped sliding grips 16, 18. The slider-crank mechanisms 12, 14 also include first and second intermediate links 20, 22 connected to the sliding grips 16, 18 by respective first and second pivotal connectors 24, 26. The pivotal connectors 24, 26 are illustrated as round bars serving as large pins which fit into bushings 25, 27 in the intermediate links.

A coupler link 30 is provided which is capable of pivoting about a stationary pivot 32 and which is pivotally connected to both intermediate links 20, 22. From this structure, translational movement of the sliding grips 16, 18 is coupled and synchronized.

Each slider-crank mechanism, for example, mechanism 12, can be conceptually visualized as an independent slider-crank mechanism by considering the stationary pivot 32 as a ground pivot. The coupler link 30 can be visualized as a first link in the slider-crank mechanism by drawing a straight line from the connection point of the ground pivot 32 to, for example, the pivotal connection between the ground pivot 32 and the intermediate link 20. The intermediate link 20 can be visualized as a follower link in the slider-crank mechanism by drawing a straight line between both pivotal connections on the face of the intermediate link 20. The sliding grip 16, restrained to slide along one axis, provides the sliding component for the slider-crank mechanism.

According to an aspect of the disclosed embodiments, the intermediate links 20, 22 pivotally connect to the coupler link 30 so as to be equidistant from the stationary link 32. The sliding grips 16, 18 are adapted for sliding on a common gripping axis 28, in both a gripping direction and a releasing direction. Moreover, a rotational axis 36 for the coupler link 30 is perpendicular to, and bisects, the gripping axis 28. This provides various results. For example, the sliding grips 16, 18 translate a same amount toward and away from the rotational axis 36 of the coupler link 30. Further, the stationary pivot 32 is level with the sliding grips 16, 18 and, as indicated, centered between the pivotal connectors 24, 26. This configuration maximizes the efficiency of the transmitted forces and torques in the system.

Regarding the shape of the coupler link 30 and the intermediate links 20, 22, the coupler link 30 includes an outer contour 38, which is illustrated as being circular. The intermediate links 20, 22 include respective first and second inner contours 40, 42, which face and mirror a portion of the coupler link outer contour 38. As such, when the sliding grips 16, 18 have advanced in the gripping direction, the inner contours 40, 42 of respective intermediate links 20, 22 nest adjacent to, with minimal clearance so as to prevent binding, the outer contour 38 of the coupler link 30.

The sliding grips 16, 18 include respective first and second sliding cylinder rods 44, 46. The cylinder rods 44, 46 include first and second surfaces 48, 50 on respective first and second gripping ends 52, 54 for mounting removable/interchangeable jaw faces and gripping specimens for material testing, such as, but not limited to, tensile testing. For example, different jaw faces could be utilized for accommodating various specimen sizes and shapes, such as round, flat, cable, etc.

In the illustration, the removable jaw faces are not disclosed. Instead, in the disclosed embodiment, centering recesses, for example, recess 51, are provided in the cylinder rods, along with orienting dowel pins, for example, dowel pin 53. This structure receives and centers a rear side of an appropriate jaw. Alternatively, the jaws can be integral with the sliding cylinder rod gripping ends 52, 54.

The sliding grips 16, 18 include first and second pistons 56, 58 fixedly positioned on respective first and second axial outer ends 60, 62, as illustrated in FIG. 2. The pistons 56, 58 urge respective cylinder rods 44, 46 in the gripping and releasing directions.

As illustrated in FIG. 2, the cylinder rods 44, 46 include respective first and second linkage overload protection structures 64, 66. The purpose of these structures 64, 66 is to decouple motion of the cylinder rods 44, 46 from respective pivotal connectors 24, 26. This decoupling would occur when, for example, an end of an off-center specimen disposed against the second slider-crank mechanism 14 prevents translational motion of the cylinder rod 46. At this point, the coupler link 30 prevents further motion in the intermediate links 20, 22 as well as the pivotal connectors 24, 26. The stated decoupling enables advancing the cylinder rod 44 in the first slider-crank mechanism 12 so as to firmly grip the end of the off-center specimen. This configuration minimizes stresses transmitted to the coupler link 30, the intermediate links 20, 22 and the pivotal connectors 24, 26.

More specifically, the linkage overload protection structures 64, 66 include first and second blind openings 68, 70 in respective cylinder rods 44, 46. The blind openings 68, 70 terminate at the gripping ends 52, 54 of respective cylinder rods 44, 46. Moreover, first and second sliding links 72, 74 are disposed within the blind openings 68, 70 of respective cylinder rods 44, 46. In addition, the sliding links 72, 74 have an outer diameter which is substantially the same as the inner diameter of respective blind openings 68, 70.

The linkage overload protection structures 64, 66 also include first and second biasing structures 76, 78, between the sliding links 72, 74 and respective pistons 56, 58. The biasing structures 76, 78, which are illustrated as springs, bias the sliding links 72, 74 against the gripping ends 52, 54 of respective cylinder rods 44, 46. This provides first and second spaces 77, 79 between the sliding links 72, 74 and respective pistons 56, 58, as illustrated in FIG. 2.

First and second cylinder rod slots 80, 82 are provided in respective cylinder rods 44, 46 and which extend parallel to the gripping axis 28. Through these slots 80, 82, the pivotal connectors 24, 26 connect with respective sliding links 72, 74. The size of the cylinder rod slots 80, 82 is greater than the combined size of the pivotal connectors 24, 26 and respective spaces 77, 79 between the sliding links 72, 74 and the pistons 56, 58.

The above structure decouples motion of the cylinder rods 44, 46 from respective pivotal connectors 24, 26 so that the mechanism 10 can grip an off-center specimen. However, the extent at which the decoupling enables effective gripping of an off-centered specimen is based on the size of the stated spacing 77, 79. Where the off-center specimen is against the second cylinder rod 46, once the piston 56 in the first cylinder rod 44 has compressed the spring 76 and connected with the sliding link 72, the cylinder rod 44 will be unable to further advance in the gripping direction. Accordingly, the spaces 77, 79 are designed around a maximum allowable bend in an off-center specimen which would reasonably provide reliable material test results.

As illustrated in FIG. 2, the sliding links 72, 74 also include first and second connector openings 84, 86 for receiving respective pivotal connectors 24, 26. First and second pins 73, 75 are threaded into the pivotal connectors 24, 26 through clearance openings at the gripping ends 52, 54 of the cylinder rods 44, 46 and through the gripping end side of respective sliding links 72, 74. As seen in the illustration, heads of the pins 73, 75 bottom out at the gripping end side of respective sliding links 72, 74. This configuration ensures that the pivotal connectors 24, 26 pivot only in the bushings 25, 27 in respective intermediate links 20, 22.

The pistons 56, 58 include respective first and second piston bosses 88, 90. The piston bosses 88, 90 have a diameter which, when threaded, are capable of being fixedly connected to respective cylinder rods 44, 46, which are also threaded. Accordingly, the piston bosses 88, 90 center and fix the pistons 56, 58 at the blind openings 68, 70 of respective cylinder rods 44, 46.

In addition to the above structure, the linkage overload protection structures 64, 66 include first and second blind openings 92, 94 in respective sliding links 72, 74. Also provided are first and second blind openings 96, 98 in respective piston bosses 88, 90. The springs 76, 78 fit between the blind openings 92, 94 in the sliding links 72, 74 and the blind openings 96, 98 in respective piston bosses 88, 90. As such, the springs 76, 78 remain fixed in place and orientation during operation.

Figure 3:
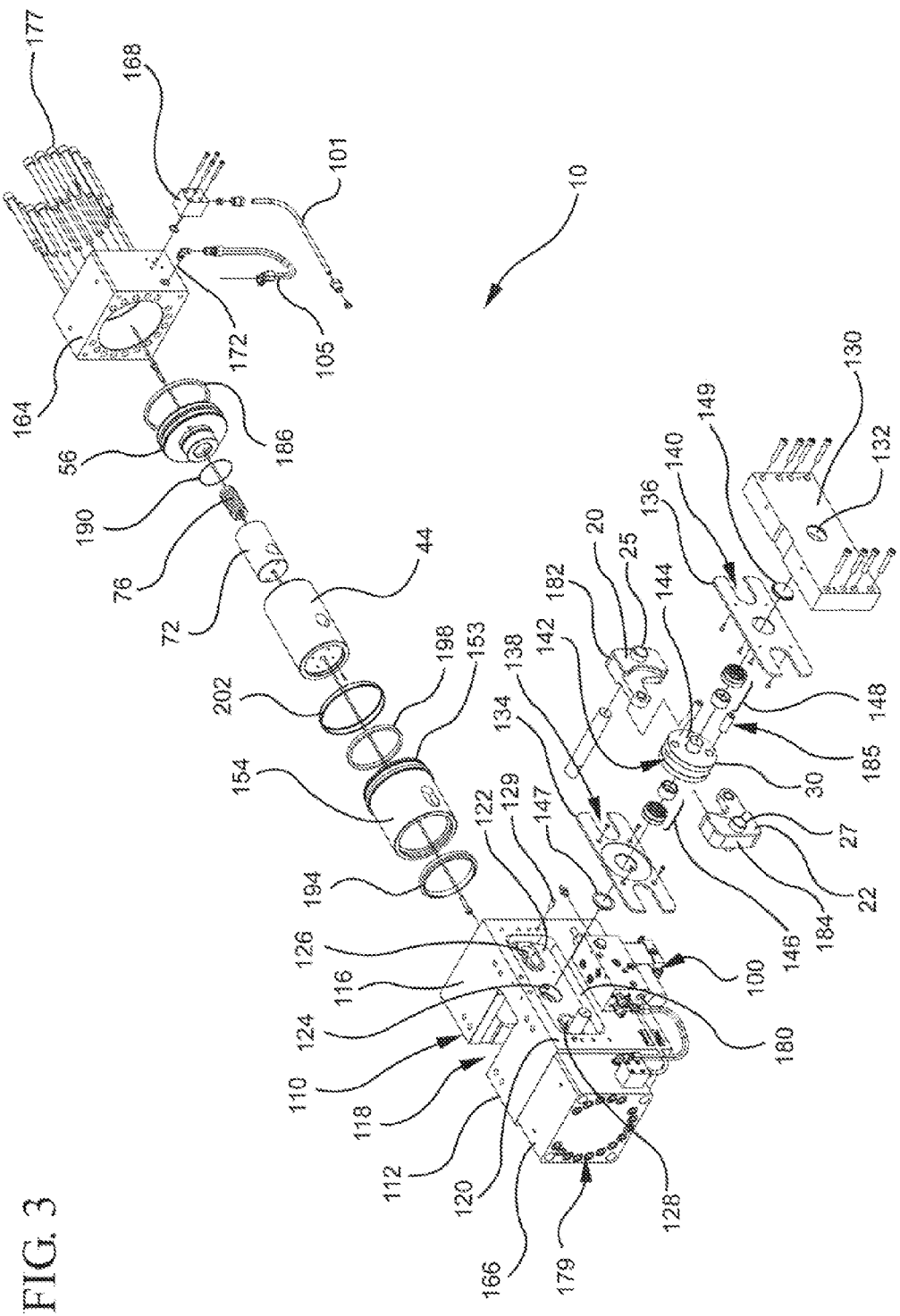
FIG. 3 illustrates an exploded view of a mechanism assembly which includes the linkage illustrated in FIG. 1 with related components and disposed within a casing.
Figure 4:
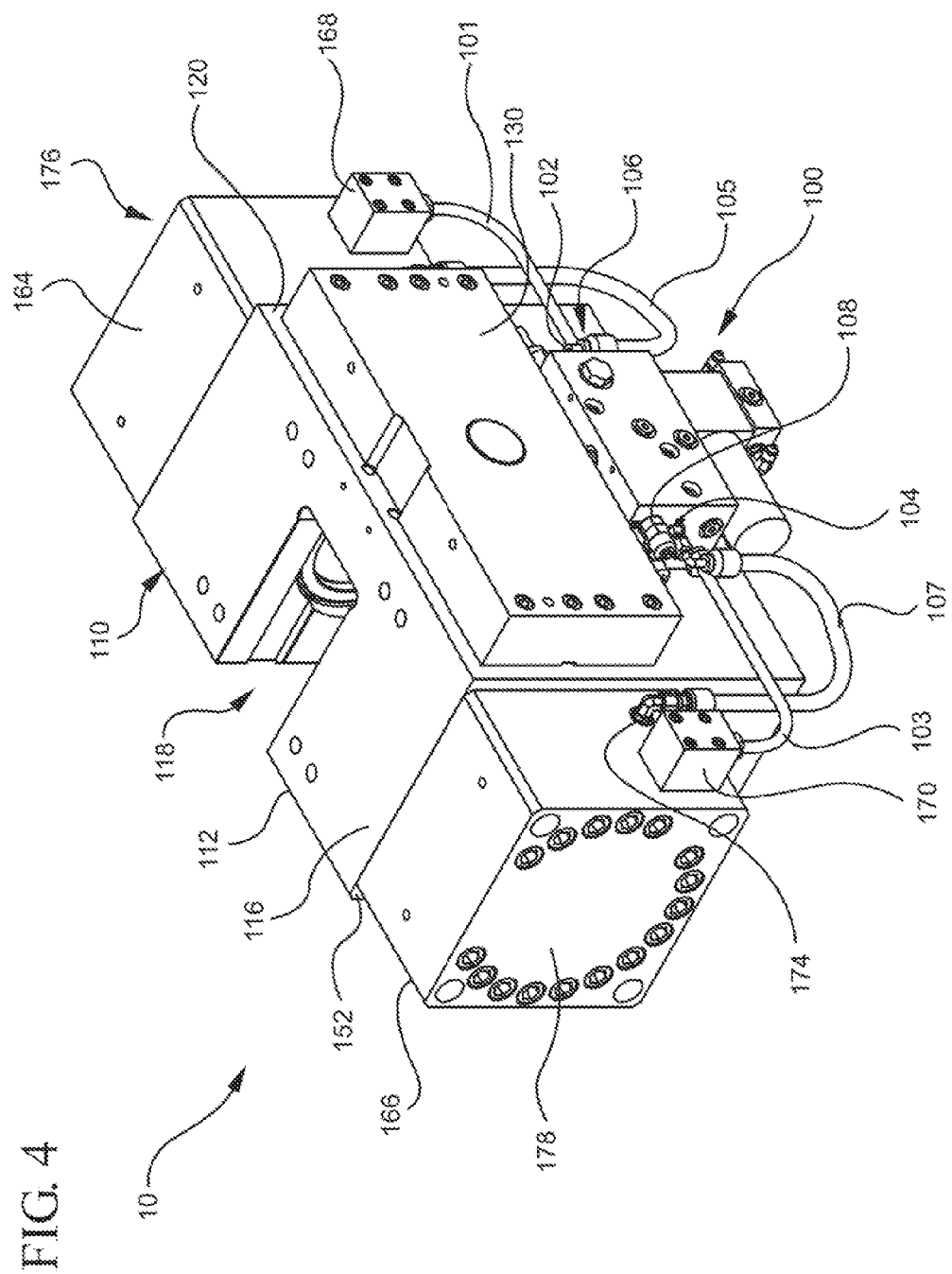
FIG. 4 illustrates a rear perspective view of the mechanism assembly illustrated in FIG. 3.

Turning to FIGS. 3-7, additional components of the mechanism 10 will be disclosed. Turning first to FIGS. 3 and 4, the mechanism 10 is provided with a hydraulic manifold 100 for actuating the pistons 56, 58. The manifold 100 includes first and second high pressure ports 102, 104 which are disposed at opposing sides of the manifold 100. Through rigid pipe connectors, for example, first and second connectors 101 and 103, the manifold 100 delivers high pressure fluid to a high pressure side of respective pistons 56, 58. Through such high pressure hydraulics, the pistons 56, 58 are driven in the gripping direction.

The manifold 100 includes first and second low pressure ports 106, 108 which are disposed adjacent to respective high pressure ports 102, 104. Through hose connectors, for example, first and second connectors 105, 107, the manifold 100 delivers low pressure fluid to a low pressure side of respective pistons 56, 58. Through such low pressure hydraulics, the pistons 56, 58 are driven in the releasing direction.

It is to be appreciated that the high pressure ports 102, 104 supply significantly higher pressure for driving the pistons 56, 58 in the gripping direction as compared with the low pressure ports 106, 108. For example, the generated gripping force can be one and a half times the tensile force on the specimen undergoing a stress/strain analysis. Such tensile forces can be 600 kilonewtons or more.

Figure 5:
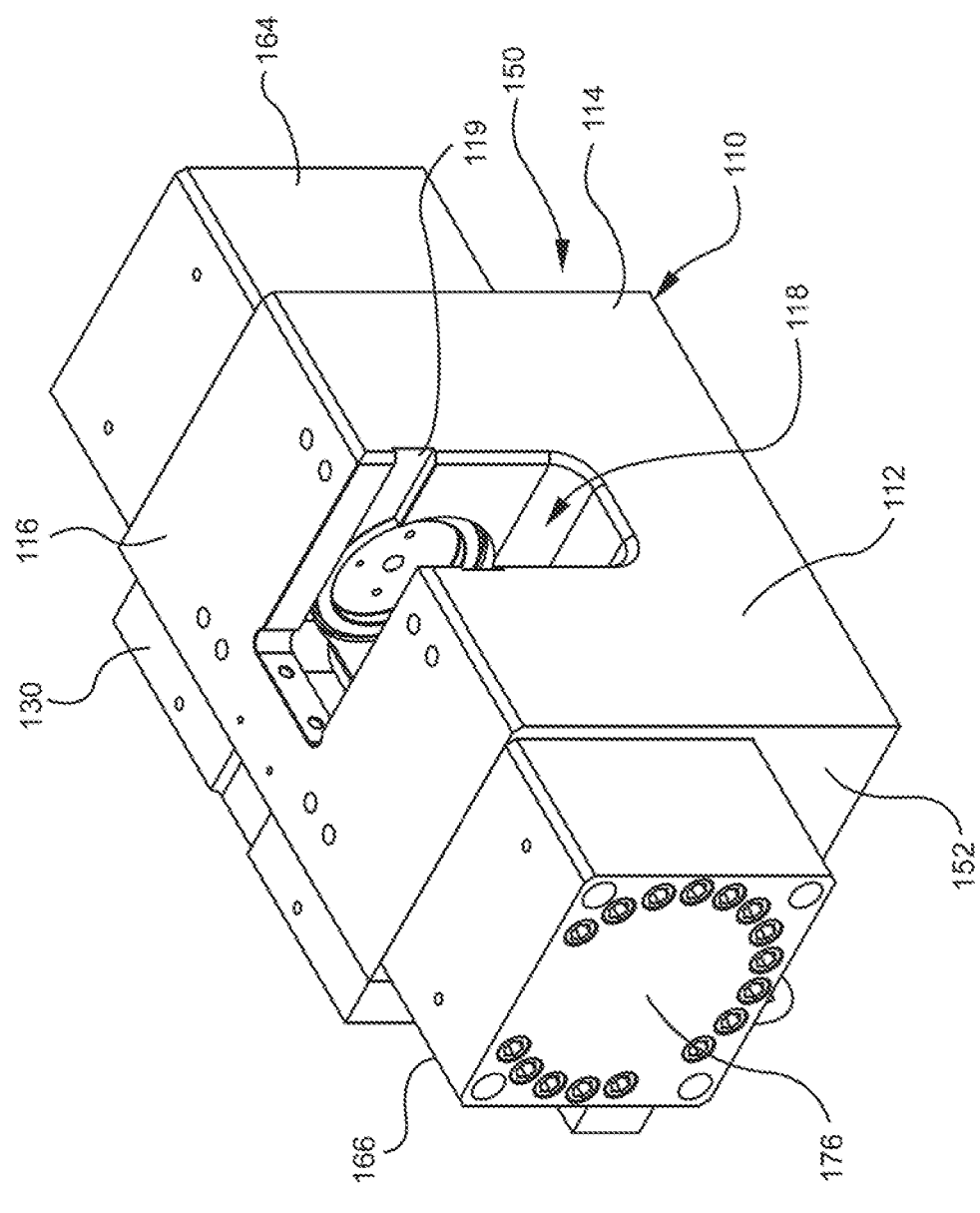
FIG. 5 illustrates a front perspective view of the mechanism assembly illustrated in FIG. 3.
Figure 6:
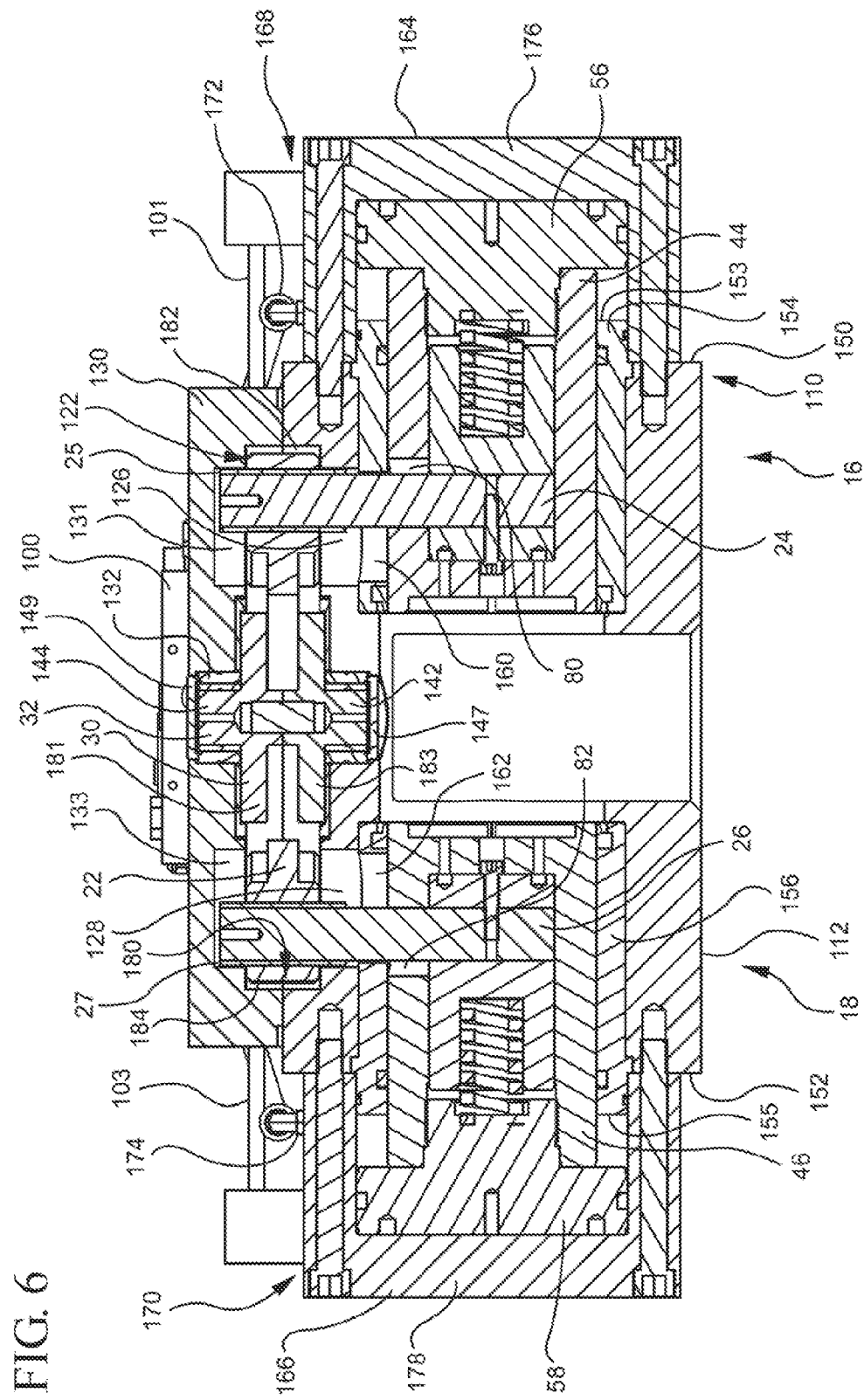
FIG. 6 illustrates a cross sectional view of the mechanism assembly illustrated in FIG. 3.

The mechanism 10 includes a mechanism casing 110 designed to house and support the above disclosed components. As illustrated in FIGS. 3-5, the casing 110 includes a central housing 112 which has first and second faces 114, 116 on which a continuous opening 118 for receiving a specimen is provided.

When a pair of mechanisms is positioned for receiving opposing ends of a specimen, as would be typically found in a materials testing environment, each mechanism 10 is oriented such that the first face 114 defines a front face. Through the front face 114, a specimen can be inserted such that the specimen extends away from the mechanism 10, through the second face 116. Accordingly, the second face will be the bottom or top face of the mechanism, depending on its mounting orientation.

Mounting, while not disclosed in detail herein, occurs via an appropriate mechanical structure on the face which opposes the second face 116 in the central housing 112. In addition, the opening 118 in the front face 114 includes a slot 119 extending parallel with the second face 116, about the inside perimeter of the opening 118. While not disclosed in full detail herein, the slot 119 is used for mounting adapter plates that allow the grips 16, 18 to be used for different types of tests, as would be familiar to one of ordinary skill.

A third face 120 of the central housing 112 defines a rear face of the mechanism 10, and this face 120 supports the hydraulic manifold 100. The rear face 120 also includes a link housing 122, illustrated in FIGS. 3 and 6, in which the coupler link 30, the intermediate links 20, 22 along with ends of the pivotal connectors 24, 26 and bushings 25, 27 are disposed throughout the operational life of the mechanism 10. In addition, the link housing 122 has a central opening 124 for seating the stationary pivot 32.

The link housing 122 includes first and second slots 126, 128. The link housing slots 126, 128 are aligned with, that is, adjacent and parallel to, respective cylinder rod slots 80, 82 enabling the pivotal connectors 24, 26 to connect with respective sliding links 84, 86. In addition, the link housing slots 126, 128 are longer than the distance traveled by respective cylinder rods 44, 46 when gripping and releasing a specimen. This configuration enables the pivotal connectors 24, 26 to translate in the gripping and releasing directions without bottoming out on opposing ends of respective link housing slots 126, 128.

Furthermore, the link housing slots 126, 128 are sized to fit the bushings 25, 27 disposed about respective pivotal connectors 24, 26. Allowing the bushings 25, 27 to extend into the link housing slots 126, 128 provides translational guidance, without binding, to respective pivotal connectors 24, 26. This in turn, provides translational guidance to the intermediate links 20, 22 at the connection with respective pivotal connectors 24, 26. This ensures that the intermediate links 20, 22 will travel in an axis which is parallel to the translational axis 28 for the sliding grips 16, 18.

The central housing 112 also includes a back plate 130 for encasing the coupler link 30 and the intermediate links 20, 22 within the link housing 122. Accordingly, the back plate 130 typically has a plan area which is larger than the area defined by the link housing 122.

The back plate 130 includes a central opening 132 serving as a secondary support for the stationary pivot 32. As such, the stationary pivot 32 is supported on both ends to secure the pivot axis 36 in place.

The back plate 130 also includes first and second back plate slots 131, 133. The back plate slots 131, 133 have the same size, shape and orientation as the link housing slots 126, 128. The back plate slots 131, 133 receive ends of the pivotal connectors 24, 26 and bushings 25, 27 which are sized to extend past the intermediate links 20, 22. With the combination of the link housing slots 126, 128 and the back plate slots 131, 133, the pivotal connectors 24, 26 are supported at two positions. This dual support secures the translational accuracy of the pivotal connectors 24, 26 and, therewith, the intermediate links 20, 22.

In addition, dowel pins, such as dowel pin 129, are provided for aligning the back plate 130 against the link housing 122 when the back plate 130 is fastened, for example, via screws, to the central housing 112. The pins ensure that the link housing slots 126, 128 and respective back plate slots 131, 133 are properly aligned during installation of the back plate 130 and during operation.

As can be appreciated from reading the above disclosure, various forms of simultaneous movements occur throughout the operational cycle of the system. Such movements include (1) translation of the cylinder rods 44, 46 along the gripping axis 28; (2) translation of the intermediate links 20, 22 in a direction parallel to the gripping axis 28; (3) pivoting of each of the intermediate links 20, 22 about connection points with respective pivotal connectors 24, 26; (4) pivoting of each of the intermediate links 20, 22 about connection points with the coupler link 30; and (5) pivoting of the coupler link 30 about the stationary pivot 32.

The above noted movements between the components can produce an operational load which causes an elastic deflection of the pivotal connectors 24, 26. Such deflection can further result in component damage due to surface to surface sliding or rotation between the intermediate links 20, 22, the pivotal connectors 24, 26, the coupler link 30, the link housing 122 and the back plate 130.

To protect against this type of potential component damage, first and second wear plates 134, 136 are provided. The wear plates 134, 136 are positioned within the link housing 122 such that the first wear plate 134 is positioned against the back face of the link housing 122. On the other hand, the second wear plate 136 is positioned against the internal side of the back plate 130.

The wear plates 134, 136 include respective first and second sets of cutouts 138, 140 as provided in FIG. 3. The sets of cutouts 138, 140 enable the stationary pivot 32 to pass therethrough. The sets of cutouts 138, 148 also enable the pivotal connectors 24, 26 to pass therethrough and translate in the gripping and releasing directions.

Furthermore, as an added benefit, the wear plates 134, 136 are field serviceable. That is, the wear plates 134, 136 can be replaced by removing the back plate 130 and the intermediate links 20, 22 at any time.

The coupler link 30 includes first and second bosses 142, 144 which extend into respective central openings 124, 132 of the link housing 122 and the back plate 130. The bosses 142, 144 are fitted with respective first and second rolling bearings 146, 148. First and second end caps 147, 149 seal the rolling bearings 146, 148 in place and protect the rolling bearings 146, 148 from the elements.

Figure 7:
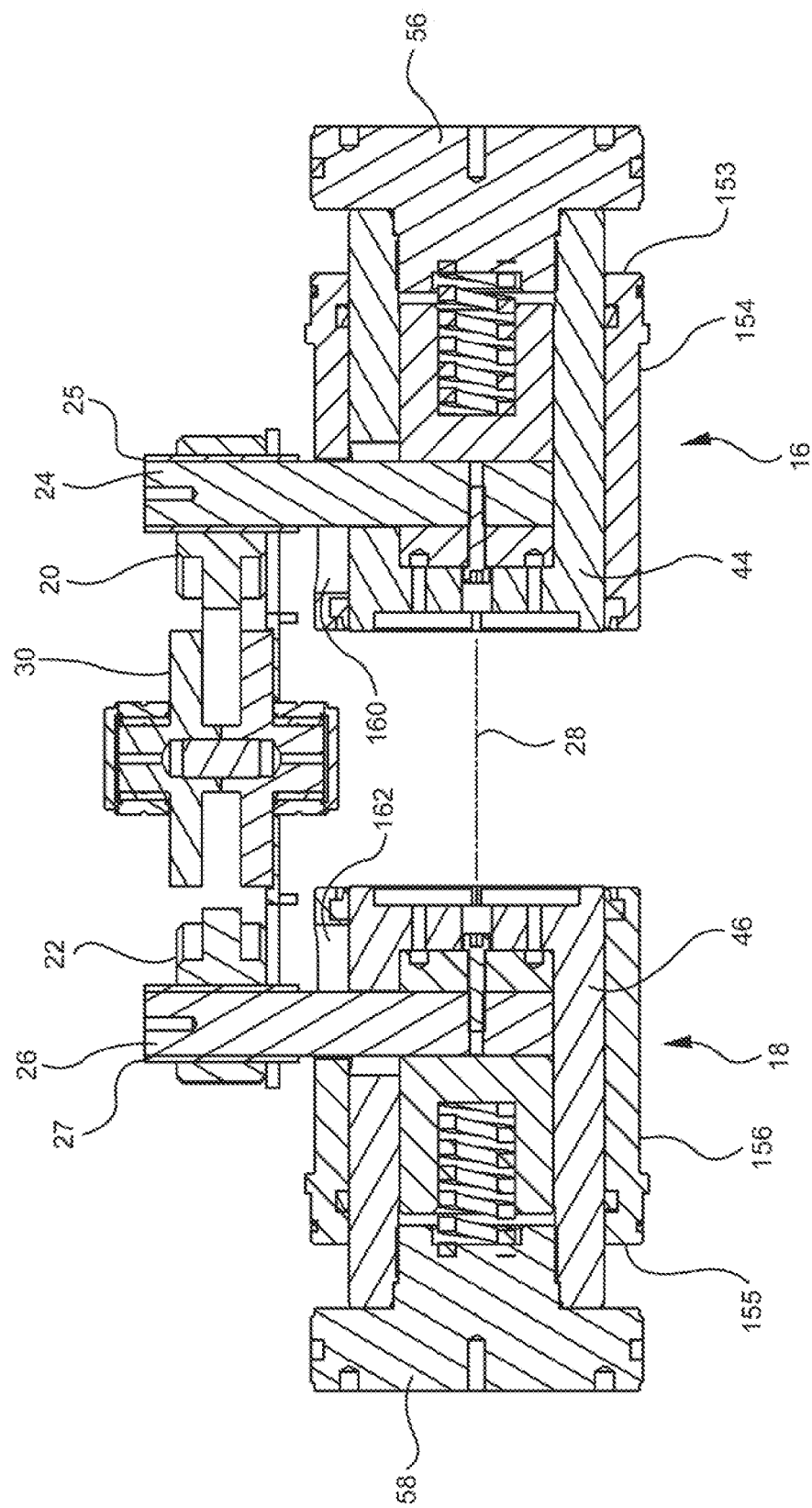
FIG. 7 illustrates a cross sectional view of the linkage illustrated in FIG. 1 and which further includes sleeves through which the components of the linkage slide during operation.

Further to the configuration of the casing 110, the central housing 112 includes first and second opposing side faces 150, 152. The side faces 150, 152 each include an opening for receiving respective first and second fixed sleeves 154, 156. FIG. 7 shows the relationship of the sleeves 154, 156 with the sliding grips 16, 18, the intermediate links 20, 22, the pivotal connectors 24, 26, and the coupler link 30.

The sleeves 154, 156 receive respective cylinder rods 44, 46, which are capable of sliding therein in the gripping and releasing directions. As can be appreciated, the positioning of the sleeves 154, 156, in the central housing 112, defines the common gripping axis 28 for the sliding grips 16, 18.

The sleeves 154, 156 include piston side ends or shoulders 153, 155, which define the maximum gripping travel of respective pistons 56, 56. That is, while the hydraulic manifold 100 can provide an operational limit on the piston gripping travel, the sleeve shoulders 153, 155 provide a physical limit to such travel.

The sleeves 154, 156 include first and second sleeve slots 160, 162. The sleeve slots 160, 162 are aligned with the link housing slots 126, 128 so that the pivotal connectors 24, 26 can pass to respective cylinder rods 44, 46 and translate in the gripping and releasing directions. The sleeve slots 154, 156 are slightly larger than the spacing traced by the radial outsides of respective pivotal connectors 24, 26. This sizing provides clearance for the translational motion of the pivotal connectors 24, 26 in the releasing and gripping directions. However, the sleeve slots 154, 156 are not as large as respective link housing slots 126, 128. This is because, as illustrated, the sleeve slots 154, 156 are not designed to receive respective bushings 25, 27.

As illustrated in FIGS. 3-6, the casing 110 includes first and second piston housings 164, 166. The piston housings 164, 166 cover the openings in the side faces 150, 152 of the central housing 112. The pistons 56, 58 are positioned in the casing 110 to remain within respective piston housings 164, 166 while translating in the gripping and releasing directions.

The piston housings 164, 166 include respective first and second high pressure ports 168, 170. The high pressure ports 168, 170 are positioned on a high pressure side of the piston housings 164, 166, for example, on the axial outer ends of respective pistons 56, 58. In this configuration, the high pressure ports 168, 170, connected to the high pressure pipes 101, 103, deliver high pressure fluid to respective pistons 56, from the hydraulic manifold 100. These connections enable translating the pistons 56, 58 in the gripping direction.

The piston housings 164, 166 also include respective first and second low pressure ports 172, 174. The low pressure ports 172, 174 are positioned on a low pressure side of the piston housings 164, 166, for example, on the axial interior ends of respective pistons 56, 58. In this configuration, the low pressure ports 172, 174, connected to the low pressure tubes 105, 107, deliver low pressure fluid to respective pistons 56, from the hydraulic manifold 100. These connections enable translating the pistons 56, 58 in the releasing direction.

The piston housings 164, 166 also include respective first and second back walls 176, 178. The back walls 176, 178 of the piston housings 164, 166 define a maximum travel of respective pistons 56, 58 in the releasing direction. That is, while the hydraulic manifold 100 can provide an operational limit on the piston travel in the unclamping direction, respective back walls 175, 178 provide a physical limit to such travel.

First and second sets of bolts 177, 179 are provided outside of both piston housings 164, 166. The sets of bolts 177, 179 are required to keep the piston housings 164, 166 in place, against the central housing 112, under the aforementioned high operational pressure from respective pistons 56, 58 during the gripping operation.

In addition to the above disclosed structural aspects of the mechanism 10, the link housing 122 in the casing 110 has an inner edge 180, which has an inner edge contour. The inner edge contour is illustrated in FIG. 3 as being substantially rectangular. On the other hand, the intermediate links 20, 22 include respective first and second outer edges 182, 184, which face a portion of the inner edge 180 of the link housing. The outer edges 182, 184 of respective intermediate links 20, 22 mirror the contour of the portion of the inner edge 180 of the link housing 122 which they face. The design is such that there is clearance, throughout operation, between the inner edge 180 of the link housing 122 and the outer edges 182, 184 of respective intermediate links 20, 22. As can be appreciated, this configuration prevents binding.

The coupler link 30 is illustrated as having first and second disks 181, 183, connected via, for example, a dowel pin, and which provide for sandwiching the connections with both intermediate links 20, 22. Furthermore, a set of pins 185 is provided for facilitating the connection between the coupler link 30 and the intermediate links 20, 22. However, the dual disk design is just one possible design for connecting the coupler link 30 with the intermediate links 20, 22.

Various seals are also provided to prevent unwanted leaking of the hydraulic fluid. For example, first and second piston seals, for example, seal 186, seal high-pressure fluid from low-pressure fluid over respective pistons 56, 58. First and second biasing structure seals, for example, seal 190, are provided on the piston bosses 88, 90 for sealing low-pressure fluid from respective biasing structures 76, 78. The sleeves 156, 158 include first and second grip-side seals, for example, seal 194, for preventing contaminants from passing between the sleeves 156, 158 and respective cylinder rods 44, 46 while releasing a specimen. First and second low-pressure side sleeve-inner diameter seals, for example, seal 198, and first and second low-pressure side sleeve-outer diameter seals, for example, seal 202, are provided for preventing low-pressure fluid from traveling into, through, or past the sleeves 156, 158 from the low pressure side of respective pistons 56, 58.

The disclosed embodiments relate to a system for providing precision mechanical synchronization of opposing hydraulic cylinder travel. The system utilizes the pair of four bar slider crank linkages configured to use the common pivot and rotating links. The axis of rotation for the rotating link is perpendicular to and bisects the collinear axis of translation for each of the slider links. Independent translation of either slider link will result in an incremental rotation of the rotating link, thereby forcing an equal and opposite translation of the other slider link.

Because of the excessive compressive forces generated by the grips, the design incorporates the spring loaded coupling system to add a controlled amount of compliance to the system protecting components from overload.

As indicated, when the system attempts to grip a rigid off-center specimen, such as a bar bent at its lengthwise center, both sides of the clamping tool will traverse towards center in a synchronized motion, due to action of the synchronization linkage, until one side makes contact and stops. Since both sides of the clamping tool are mechanically coupled through the synchronizer mechanism, substantially no motion is possible and the system will stall.

Assuming that the specimen does not yield, pressure will continue to build as the system attempts to maintain balance. Without the disclosed linkage overload protection structure, the synchronizing linkage could be subjected to loads capable of causing component failure. Due to the magnitude of the force generated, it is not practical to design synchronizing linkage components capable of carrying this load. Instead, the disclosed linkage overload protection structure provides the system with a designed compliance, allowing the synchronizing linkage to decouple from the clamping travel once a predetermined load is reached. This breakaway load can be tuned with various spring rates and preloads to match the requirements of the specimen grip and provide controlled protection of the synchronizer linkage.

Accordingly, the disclosed embodiment provides a robust solution to the engineering challenge of synchronizing the travel of opposing hydraulic cylinders. It provides accurate and repeatable clamping of test specimens without the complication associated with a rack and pinion configuration. The synchronizing linkage includes simple to machine components that are relatively easy to assemble. The individual links are assembled with simple cylindrical (pin to bushing) press fit connections. The unit is field serviceable and requires essentially no periodic adjustments.

By design, the linkage style synchronizing linkage is less affected by contamination because of no meshing components to become filled with debris. As disclosed, the synchronization linkage is located in a sealed compartment outside the clamping area offering additional protection from test environment contamination. The durable crank slider linkage component of the synchronizing linkage is capable of carrying loads in excess of a typical rack and pinion system, occupying the same packaging envelope, would be predicted to handle. In addition, the durability of this design is enhanced by the spring loaded linkage overload protection structure, which protects the mechanical synchronizer linkage.

The present invention may be embodied in other specific forms without departing from its spirit or essential characteristics. The described embodiments are to be considered in all respects only as illustrative and not as restrictive. The scope of the invention is, therefore, indicated by the appended claims and their combination in whole or in part rather than by the foregoing description. All changes that come within the meaning and range of equivalency of the claims are to be embraced within their scope.

I claim:

1. A synchronized gripping mechanism, comprising:
   first and second slider-crank mechanisms, each including a sliding grip and an intermediate link connected by a pivotal connector; and
   the synchronized gripping mechanism further including a coupler link capable of pivoting about a stationary pivot and connected to each intermediate link;
   the pivotal connectors including bushings traveling within and with respect to fixed stationary elongated link housing slots providing translational guidance to the intermediate links at connections with the pivotal connectors; and
   whereby translational movement of each sliding grip is coupled and synchronized.

2. The mechanism of claim 1, wherein:
   each intermediate link is connected to the coupler link so as to be equidistant from the stationary pivot;
   each sliding grip is adapted for sliding on a common gripping axis in both a gripping direction and a releasing direction; and
   a rotational axis for the coupler link is perpendicular to and bisects the gripping axis.

3. A synchronized gripping mechanism, comprising:
   first and second slider-crank mechanisms, each including a sliding grip and an intermediate link connected by a pivotal connector; and
   the synchronized gripping mechanism further including a coupler link capable of pivoting about a stationary pivot and connected to each intermediate link;
   whereby translational movement of each sliding grip is coupled and synchronized;
   wherein each intermediate link is connected to the coupler link so as to be equidistant from the stationary pivot, each sliding grip is adapted for sliding on a common gripping axis in both a gripping direction and a releasing direction, and a rotational axis for the coupler link is perpendicular to and bisects the gripping axis; and
   wherein each sliding grip further comprises a sliding cylinder rod which includes a gripping end and a piston fixedly positioned on an opposing end, where the piston urges the cylinder rod in the gripping and releasing directions.

4. The mechanism of claim 3, wherein each cylinder rod includes a linkage overload protection structure which is capable of decoupling motion of each cylinder rod from each respective pivotal connector.

5. The mechanism of claim 4, wherein each linkage overload protection structure includes:
   a blind opening in the cylinder rod, terminating at the gripping end of the cylinder rod;
   a sliding link disposed within the blind opening of the cylinder rod;
   a biasing structure between the sliding link and the piston for biasing the sliding link against the gripping end of the cylinder rod, thereby spacing the sliding link from the piston; and
   a cylinder rod slot in the cylinder rod which extends parallel to the gripping axis and through which the pivotal connector connects with the sliding link, the size of the cylinder rod slot being greater than the combined size of the pivotal connector and the spacing between the sliding link and the piston;
   whereby, motion of each cylinder rod is capable of being decoupled from each respective pivotal connector.

6. The mechanism of claim 5, wherein each sliding link includes a connector opening for receiving the pivotal connector, and each pivotal connector is a pin, which is pivotally connected to the intermediate link and further fixed to the sliding link.

7. The mechanism of claim 5, wherein each piston includes a piston boss for centering and fixing the piston at the blind opening of the cylinder rod.

8. The mechanism of claim 7, wherein each linkage overload protection structure includes a blind opening in the sliding link and a blind opening in the piston boss, and where the biasing structure is a spring which fits between the blind opening in the sliding link and the blind opening in the piston boss.

9. The mechanism of claim 5, wherein the mechanism further comprises a hydraulic manifold for actuating each piston, which includes:

first and second high pressure ports adapted for communicating high pressure fluid to a high pressure side of each piston for driving each piston in the gripping direction; and first and second low pressure ports adapted for communicating low pressure fluid to a low pressure side of each piston for driving each piston in the releasing direction.

10. The mechanism of claim 5, wherein the mechanism further comprises a mechanism casing, which includes a central housing, and the central housing comprises first and second faces which include a continuous specimen opening for receiving one end of a specimen.

11. The mechanism of claim 10, wherein a third face of the central housing, which defines a rear face of the mechanism, includes a link housing in which the coupler link and each intermediate link are disposed; and the link housing includes:
a central opening for seating the stationary pivot; and
first and second slots, each being aligned with each respective cylinder rod slot such that each pivotal connector is capable of passing through each respective cylinder rod slot;
wherein each link housing slot serves as a translational guide for each respective pivotal connector when translating in the gripping and releasing directions.

12. The mechanism of claim 11, wherein the central housing includes a back plate for encasing the coupler link and each intermediate link within the link housing, and the back plate includes a central opening serving as is a secondary support for the stationary pivot.

13. The mechanism of claim 12, wherein:
the back plate includes first and second slots which are aligned with and have substantially a same shape as each respective link housing slot; and
said back plate slots serving as a secondary support for each respective pivotal connector such that said back plate slots, with said link housing slots, serve as the translational guide for each respective pivotal connector when translating in the gripping and releasing directions.

14. The mechanism of claim 12, wherein the mechanism further comprises:
first and second wear plates positioned within the link housing such that the first wear plate is against a back face of the link housing and the second wear plate is against the back plate; and
the wear plates each include cutouts enabling the stationary pivot to pass therethrough and each pivotal connector to pass therethrough and translate in the gripping and releasing directions.

15. The mechanism of claim 12, wherein the coupler link includes first and second bosses respectively extending into the central openings of the link housing and the back plate, and the first and second bosses are fitted with respective first and second rolling bearings.

16. The mechanism of claim 15, wherein:
the central housing includes first and second opposing side faces, each including an opening for receiving a fixed sleeve, each sleeve receiving a respective one of the cylinder rods, which is capable of sliding therein in the gripping and releasing directions; and
each sleeve including a sleeve slot aligned with each respective link housing slot, each sleeve slot enabling each pivotal connector to pass into each respective cylinder rod slot and translate in the gripping and releasing directions;
wherein the fixed sleeves define the common gripping axis for the sliding grips.

17. The mechanism of claim 16, wherein the casing further includes first and second piston housings which cover the openings in the first and second side faces of the central housing, such that each piston travels in a respective piston housing while translating in the gripping and releasing directions.

18. The mechanism of claim 17, wherein each sleeve includes a shoulder defining a travel limit for each piston in the gripping direction and each piston housing includes a back wall defining a travel limit for each piston in the releasing direction.

19. The mechanism of claim 17, wherein each piston housing includes:
a high pressure port positioned on a high pressure side of the piston housing so that high pressure fluid is communicated to the piston for translating the piston in the gripping direction; and
a low pressure port positioned on a low pressure side of the piston housing so that low pressure fluid is communicated to the piston for translating the piston in the releasing direction.

20. The mechanism of claim 19, wherein:
each piston includes:
a piston seal for sealing high-pressure fluid from low-pressure fluid over the piston;
a biasing structure seal for sealing low-pressure fluid from the biasing structure; and
each sleeve includes:
a grip-side seal for preventing contaminants from passing between the sleeve and the cylinder rod while releasing a specimen; and
a low-pressure side sleeve-inner diameter seal and a low-pressure side sleeve-outer diameter seal, preventing low-pressure fluid from traveling into, through or past the sleeve from the low pressure side of the piston.

* * * * *